(12) United States Patent
DeSantis et al.

(10) Patent No.: US 8,152,775 B2
(45) Date of Patent: Apr. 10, 2012

(54) ACCESS PORT USING SHAPE ALTERING ANCHOR

(75) Inventors: Robert J. DeSantis, Redding, CT (US); Jason Sung, North Branford, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/193,928

(22) Filed: Aug. 19, 2008

(65) Prior Publication Data

US 2009/0105655 A1 Apr. 23, 2009

Related U.S. Application Data

(60) Provisional application No. 60/980,576, filed on Oct. 17, 2007.

(51) Int. Cl.
*A61M 5/32* (2006.01)
(52) U.S. Cl. ..................................... 604/174
(58) Field of Classification Search ............... 604/174, 604/114, 95.01, 530, 533; 600/466
See application file for complete search history.

(56) References Cited

U.S. PATENT DOCUMENTS

| 3,729,008 A * | 4/1973 | Berkovits ............... 607/125 |
| 3,890,977 A * | 6/1975 | Wilson ................... 604/531 |
| 4,321,002 A | 3/1982 | Froehlich |
| 4,719,917 A | 1/1988 | Barrows et al. |
| 5,279,564 A * | 1/1994 | Taylor ..................... 604/104 |
| 5,468,248 A | 11/1995 | Chin et al. |
| 5,882,340 A | 3/1999 | Yoon |
| 6,235,869 B1 | 5/2001 | Roby et al. |
| 6,388,043 B1 | 5/2002 | Langer et al. |
| 6,626,916 B1 | 9/2003 | Yeung |
| 2002/0095169 A1 | 7/2002 | Maitland et al. |
| 2003/0236445 A1 * | 12/2003 | Couvillon, Jr. ............. 600/114 |
| 2003/0236531 A1 | 12/2003 | Couvillon |
| 2003/0236533 A1 | 12/2003 | Wilson et al. |
| 2004/0138702 A1 | 7/2004 | Peartree et al. |
| 2004/0230282 A1 * | 11/2004 | Cates et al. ............... 607/126 |
| 2005/0082826 A1 * | 4/2005 | Werth ....................... 285/243 |
| 2005/0149062 A1 | 7/2005 | Carroll |
| 2005/0273138 A1 * | 12/2005 | To et al. ................... 606/219 |
| 2007/0038238 A1 | 2/2007 | Freeman et al. |
| 2007/0106319 A1 | 5/2007 | Au et al. |
| 2007/0203517 A1 * | 8/2007 | Williams et al. ........... 606/191 |
| 2007/0208276 A1 | 9/2007 | Kornkven Volk et al. |
| 2007/0225651 A1 * | 9/2007 | Rosenberg et al. ........ 604/174 |

FOREIGN PATENT DOCUMENTS

EP 0 326 426 A2 8/1989

(Continued)

OTHER PUBLICATIONS

Lendlein, et al., "Shape-memory polymers as stimuli-sensitive implant materials", *Clinical Hemorheology and Microcirculation* 2005, 32:105-116.

(Continued)

*Primary Examiner* — Kevin C Sirmons
*Assistant Examiner* — Brandy C Scott

(57) ABSTRACT

The present disclosure provides access ports for use in surgery. The access ports possess a distal end which adopts an alternate shape upon the application of energy, thereby securing the access port to tissue. Alternatively, the access port may have barbs on a surface thereof which are formed upon the application of energy, thereby securing the access port to tissue.

18 Claims, 3 Drawing Sheets

FOREIGN PATENT DOCUMENTS

| | | |
|---|---|---|
| EP | 1747759 | 1/2007 |
| EP | 1747772 | 1/2007 |
| WO | WO 02/00286 | 1/2002 |
| WO | WO 03/088818 A2 | 10/2003 |
| WO | WO 03/088846 A1 | 10/2003 |
| WO | WO 2004/052594 | 6/2004 |
| WO | WO 2004/060463 | 7/2004 |
| WO | WO 2004/105621 | 12/2004 |
| WO | WO 2005/000001 | 1/2005 |
| WO | WO 2007/038715 | 5/2007 |

OTHER PUBLICATIONS

Lendlein, et al., "Biodegradable, Elastic Shape-Memory Polymers for Potential Biomedical Applications", *Science* 2002, 296:1673-1676.

Lendlein, "Solving a knotty problem—surgical sutures from shape memory polymers", *Materials World* 2002, 10(7):29-30.

Small, et al., "Laser-activated shape memory polymer intravascular thrombectomy device", *Optics Express* 2005, 13(20):8204-8213.

Faré, et al., "In vitro interaction of human fibroblasts and platelets with a shape-memory polyurethane", *Fibroblast/Platelet Interaction With SMPu* Wiley Periodicals, Inc. (2005), pp. 1-11.

International Search Report from Application No. EP 07 25 2537 dated Nov. 8, 2007.

International Search Report from European Application No. EP 08 25 3353 dated Feb. 4, 2009.

International Search Report from European Application No. EP 08 25 3356 mailed Apr. 8, 2009.

European Search Report for corresponding EP 08253364 date of mailing is Aug. 6, 2009 (3 pages).

European Search Report corresponding to European Application No. EP 10 00 5418.8, completed Jun. 24, 2010, mailed Jul. 1, 2010; 5 pages.

European Search Report for Application No. EP 08 25 3618 dated Jul. 25, 2011.

\* cited by examiner

ACCESS PORT USING SHAPE ALTERING ANCHOR

CROSS-REFERENCE TO RELATED APPLICATIONS

This application claims the benefit of and priority to U.S. Provisional Patent Application No. 60/980,576, filed Oct. 17, 2007, the entire disclosure of which is incorporated by reference herein.

TECHNICAL FIELD

The present disclosure provides access ports for use in surgical procedures and, more particularly, to an anchoring access port possessing a material on or as a part thereof which alters its configuration upon the application of energy to anchor the access port to tissue upon insertion in a patient's body. Methods of using such an access port are also provided.

BACKGROUND

During laparoscopic procedures, cannulas are utilized to provide an access port for surgical instruments and a conduit for introducing insufflation gases into the body cavity. In embodiments, a sharp trocar may be positioned within the cannula and utilized to puncture or pierce the tissue or abdominal wall. Thereafter the trocar may be removed, leaving the cannula in place and insufflation gases forced into the body cavity to form an anatomical operating space. Retention of access ports such as cannulas during a laparoscopic procedure is very important, as the ports can be accidentally ejected from the patient, resulting in inconvenience to the surgeon, loss of pneumoperitoneum, and increased procedure time.

In order to prevent an access port such as a cannula from migrating in or out through the incision, some access ports may be provided with anchoring structures to prevent the port from slipping out of the incision. For example, balloons have been used in some devices to assist in anchoring a cannula, as disclosed in U.S. Pat. No. 5,468,248 and U.S. Patent Application Publication No. 2004/0138702, the entire disclosures of each of which are incorporated by reference herein. However, unless the anchoring structure is firmly secured against the tissue, leakage of insufflation gases may occur. Thus, means for anchoring access ports to secure the access port to the tissue and prevent leakage of insufflation gases remain desirable.

SUMMARY

The present disclosure provides access ports for use in surgery, which may be configured to adopt alternate shapes upon the application of energy, thereby securing the access port to tissue.

In embodiments, an access port of the present disclosure may include a longitudinally extending shaft surrounding a central working passage, and at least one material capable of changing its configuration to form an anchoring member on at least a portion of the access port.

Suitable materials which may be utilized to form an anchoring member include, shape memory polymers, shape memory metals, shape memory alloys, electroactive polymers, combinations thereof, and the like. Materials utilized to form an anchoring member may be applied to an outer surface of the access port, or may be utilized to form the access port itself.

In embodiments, a distal end of the shaft of the access port may include the anchoring member. A material capable of changing its configuration may be secured to the distal end of the shaft chemically, physically, or combinations thereof. In embodiments, the material capable of changing its configuration may be applied to an outer surface of the shaft as a layer, with a distal end of the material capable of changing its configuration extending beyond the distal end of the shaft.

In embodiments, the anchoring member may have a permanent shape that is curved and a temporary shape that is straight.

In other embodiments, an access port of the present disclosure may include an anchoring member including barbs which have a permanent shape forming angular projections from a surface of the access port, and a temporary shape including a smooth, flat surface that is flush with the surface of the access port.

Methods for utilizing access ports of the present disclosure are also provided.

DETAILED DESCRIPTION

Figure 1A:
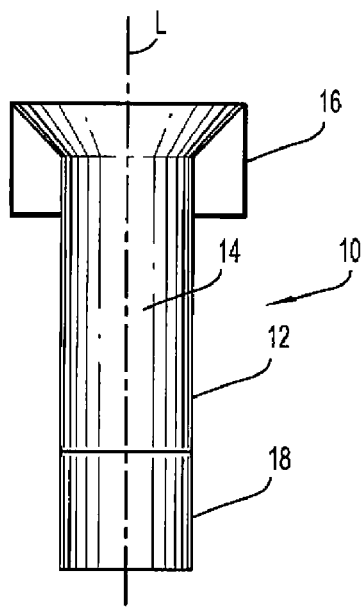
FIGS. 1A and 1B illustrate an access port of the present disclosure which has segments at the distal end formed of materials which alter their configuration upon the application of energy thereto.

The present disclosure provides an anchoring access port including an access port body having a distal end formed of a material capable of changing its shape upon the application of energy. Suitable materials which may be utilized to form the distal end of an access port of the present disclosure may alter their configuration or shape upon the application of energy such as electricity or heat, including body heat, to secure an access port within the body. Such materials include, for example, shape memory polymers, shape memory metals, shape memory alloys, electroactive polymers, combinations thereof, and the like.

In embodiments, shape memory materials may be utilized to form the anchoring member on an access port of the present disclosure. Such shape memory materials possess a permanent shape and a temporary shape. In embodiments, the temporary shape is of a configuration which enhances the ability of one to introduce an access port possessing an anchoring member into a patient's body, while the permanent shape is of a configuration which enhances the retention of the access port at the site of an incision. Suitable shape memory polymeric materials which may be utilized to fashion an anchoring member include, for example, polyurethanes, poly(styrene-butadiene) block copolymers, polynorbornenes, caprolactones, dioxanones, diol esters including oligo (epsilon caprolactone) diol, lactic acid, lactide, glycolic acid, glycolide, ether-ester diols including oligo (p-dioxanone) diol, carbonates including trimethylene carbonate, combinations thereof, and the like. In embodiments, the shape memory polymer may be a copolymer of two components with different thermal characteristics, such as oligo (epsilon-caprolactone) dimethacrylates and butyl acrylates including poly(epsilon-caprolactone) dimethacrylate-poly (n-butyl acrylate), or a diol ester and an ether-ester diol such as oligo (epsilon caprolactone) diol/oligo (p-dioxanone) diol copolymers. These multi-block oligo (epsilon-caprolactone) diol/oligo (p-dioxanone) diol copolymers possess two block segments: a "hard" segment and a "switching" segment linked together in linear chains. Such materials are disclosed, for example, in Lendlein, "Shape Memory Polymers-Biodegradable Sutures," Materials World, Vol. 10, no. 7, pp. 29-30 (July 2002), the entire disclosure of which is incorporated by reference herein.

In other embodiments, blends of materials may be utilized as the shape memory polymeric material including, but not limited to, urethanes blended with lactic acid and/or glycolic acid, homopolymers thereof or copolymers thereof, and acrylates blended with caprolactones such as polycaprolactone dimethacrylate poly(butyl acrylate) blends, and combinations thereof.

Other examples of these shape memory polymers and methods for forming permanent and temporary shapes therewith are set forth in Lendlein et al., "Shape memory polymers as stimuli-sensitive implant materials," Clinical Hemorheology and Microcirculation, 32 (2005) 105-116, and Lendlein et al., "Biodegradable, Elastic Shape-Memory Polymers for Potential Biomedical Applications," Science, Vol. 269 (2002) 1673-1676, the entire disclosures of each of which are incorporated by reference herein.

The shape memory polymeric materials of the present disclosure may, in embodiments, be configured to have a straight temporary shape and a curved permanent shape. Thus, an access port possessing a distal end or segment formed of a shape memory polymeric material may have a straight shape facilitating its insertion into tissue and, after the application of suitable energy, may return to its curved permanent shape which facilitates the retention of an access port of the present disclosure in vivo.

In embodiments, a molding process may be utilized to produce the anchoring member of the present disclosure. Plastic molding methods may be employed and may include, but are not limited to, melt molding, solution molding and the like. Injection molding, extrusion molding, compression molding and other methods can also be used as the melt molding technique. Once placed in the mold with the proper dimensions, the anchoring member may be heated to a suitable temperature, in embodiments at a temperature referred to as the permanent temperature ($T_{perm}$) which may, in embodiments, be the melting temperature of the shape memory polymeric material utilized to form the anchoring member. Heating of the anchoring member may be at suitable temperatures including, for example, from about 40° C. to about 180° C., in embodiments from about 45° C. to about 60° C., for a period of time from about 10 minutes to about 60 minutes, in embodiments from about 15 minutes to about 20 minutes, to obtain the permanent shape and dimensions of the anchoring member, including its desired curvature.

After the anchoring member with the desired thickness and curvature has been formed, the anchoring member may be deformed at a deforming temperature to obtain a straight temporary shape. There are no particular limitations on the manner in which the deformation can be achieved. Deformation can be achieved either by hand or by way of a suitable device selected to provide the desired straightness to the anchoring member.

Suitable temperatures for deformation will vary depending on the shape memory polymer utilized, but generally may be above the transition temperature of the polymer ($T_{trans}$), but below the $T_{perm}$. In embodiments, the shape memory polymer may be cooled from its $T_{perm}$ to a lower temperature which remains above the $T_{trans}$ and deformed, to a straight temporary shape.

The temperature for deformation treatment of the anchoring member molded with a previously memorized shape is one that makes possible ready deformation without producing cracks and should not exceed the temperature adopted for the shape memorization (e.g., $T_{perm}$). Deformation treatment at a temperature exceeding that for the original shape memorization may cause the object to memorize a new deformed shape.

In other embodiments, the anchoring member may be straightened to its temporary shape and cooled to room temperature (about 20° C. to about 25° C.) to obtain its temporary shape, although the temperature may differ depending upon the particular polymer employed. The anchoring member may then be cooled to a temperature below $T_{trans}$, at which time the anchoring member of the present disclosure may be affixed to, or utilized in the manufacture of, the distal end of an anchoring access port as described above. As the $T_{trans}$ is usually greater than room temperature, in embodiments cooling to room temperature may be sufficient to form the temporary shape.

The anchoring member may be deformed to its temporary shape prior to its attachment to the access port or, in other embodiments, the anchoring member may be deformed to its temporary shape after attachment to the access port. An anchoring member may be secured to an access port by any method, including the use of chemical methods, physical methods, combinations thereof, and the like, such as adhesives, sealants, glues, and the like or, in some embodiments, the use of locking rings located on the proximal and distal sides of the anchoring member at the distal end of an access port. In other embodiments, the anchoring member may be compressed to a dimension fitting within a recess or shallow depression on the surface of the distal end of the access port. Molding techniques may also be utilized to attach an anchoring member of the present disclosure to a distal end of an access port. In embodiments, the anchoring member may be affixed to the shaft of an access port so that the distal end of the anchoring member projects beyond the distal end of the access port. As noted above, in other embodiments, the shape memory material may be utilized to form the access port itself. Thus, in some embodiments, the anchoring member may be formed by machining or molding the shape memory polymer itself.

The anchoring member thus prepared recover their originally memorized permanent curved shapes on heating, either by placement in a patient's body or the addition of exogenous heat at a prescribed temperature, in embodiments above $T_{trans}$ for the shape memory polymer utilized.

Other shape memory materials, including shape memory metals and metal alloys such as Nitinol, may be used to form the anchoring member.

In order to keep the shape and thickness of the anchoring member in its temporary shape, the shape-memory anchoring member of the present disclosure should be stored at a temperature which will not cause plastic deformation of the polymers or premature switching to their permanent shape. In embodiments, the shape-memory anchoring member may be stored in a refrigerator.

As the anchoring member of the present disclosure are utilized in a living body, heating with body heat (about 37° C.)

is possible. In such a case, the temperature for shape memorization should be as low as possible and the recovery of the memorized shape may occur fairly slowly.

However, in some embodiments a higher shape-memory temperature may be desirable in order to make the shape recover at a slightly higher temperature than body temperature. Thus, in some cases releasing the anchoring member from deformation to recover the originally memorized curved shape can be achieved by heating. On heating at a temperature from about 30° C. to about 50° C., in embodiments from about 39° C. to about 43° C., the temporary straight shape may be released and the memorized permanent curved shape recovered. The higher the temperature for heating, the shorter the time for recovery of the originally memorized shape. The method for this heating is not limited. Heating can be accomplished by using a gas or liquid heating medium, heating devices, ultrasonic waves, or the like. Of course, in an application involving a living body, care may be taken to utilize a heating temperature which will not cause burns. When a liquid heating medium is used, physiological saline solution or alcohol may be desirable.

Upon insertion into the incision, the anchoring member made of a shape memory material may adopt their permanent curved configuration to assist in forming the anchoring member capable of anchoring an access port at the site of incision, either by the heat of the patient, the application of heat from an exogenous source. In embodiments, where a shape memory polymer is utilized, the heat of the body (about 37° C.), may be sufficient for the anchoring member to form their permanent anchoring shape. In other embodiments, heat may be applied to the anchoring member, in embodiments from about 39° C. to about 43° C. (just above human body temperature), to enhance the return of the shape memory polymer to its permanent anchoring shape.

Similarly, in other embodiments electrically active polymers, also known as electroactive polymers, which can alter their configuration upon application of electricity, may be utilized to fashion an anchoring member to secure an access port within the body. Suitable examples of electroactive polymers include poly(aniline), substituted poly(aniline)s, polycarbazoles, substituted polycarbazoles, polyindoles, poly (pyrrole)s, substituted poly(pyrrole)s, poly(thiophene)s, substituted poly(thiophene)s, poly(acetylene)s, poly(ethylene dioxythiophene)s, poly(ethylenedioxypyrrole)s, poly(p-phenylene vinylene)s, and the like, or combinations including at least one of the foregoing electroactive polymers. Blends or copolymers or composites of the foregoing electroactive polymers may also be used.

Similar to the change in shape which a shape memory material may undergo upon the application of energy, such as heat, in embodiments an electroactive polymer may undergo a change in shape upon the application of electricity from a low voltage electrical source (such as a battery). Electricity may also be utilized, in embodiments, to promote the change in shape of a shape memory alloy such as Nitinol. Suitable amounts of electricity which may be applied to effect such change will vary with the electroactive polymer or shape memory alloy utilized, but can be from about 5 volts to about 30 volts, in embodiments from about 10 volts to about 20 volts. The application will result in the anchoring member constructed of the electroactive polymer to change its shape from a straight, flat configuration to a curved anchoring structure capable of anchoring an access port at the site of an incision.

While an electroactive polymer does not have the same permanent shape and temporary shape as those terms are described above with respect to shape memory polymers, as used herein the term "permanent shape" as applied to an electroactive polymer may refer to, in embodiments, the shape the electroactive polymer adopts upon the application of electricity, and the term "temporary shape" as applied to an electroactive polymer may refer to, in embodiments, the shape the electroactive polymer adopts in the absence of electricity.

There is also disclosed a method of securing an access port to tissue which includes providing the disclosed access port. The access port is inserted through an incision in the tissue to position the anchoring member in the opening, and the anchoring member is activated by the application of heat, such as body heat, or electricity to assist in the retention of the access port during a laparoscopic procedure. A shape memory polymer may return to its temporary shape upon removal of heat. Where an electroactive polymer or a shape memory alloy such as Nitinol is used to form the anchoring member, the polymer or Nitinol could return to its original shape once the energy source is disconnected, thereby requiring a much lower withdrawal force to remove the access port from a patient's body.

FIG. 1A illustrates an access port 10 of the present disclosure possessing a distal end formed of material capable of altering its configuration thereby forming an anchoring member. The access port 10 possesses a longitudinally extending shaft 12 surrounding a central working passage 14. Access port 10 and shaft 12 may be formed of any material. Proximal end 16 of access port 10 is wider than the distal end of access port 10. A distal end 18 of said access port is formed of a material capable of changing its configuration thereby forming an anchoring member. Materials which may be utilized to form distal end 18 include a shape memory material or electroactive polymer. As depicted in FIG. 1A, distal end 18 possesses a straight, flat configuration thereby facilitating the insertion of access port 10 into tissue.

Figure 1C:
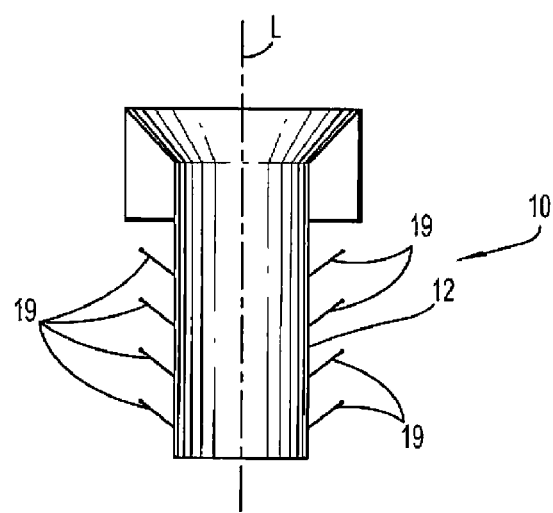
FIG. 1C is an alternate embodiment of an access port of the present disclosure possessing barbs to further enhance retention of the access port in tissue.

FIG. 1C illustrates an alternate embodiment of an access port 10 of the present disclosure possessing shaft 12 and distal end 18, with barbs 19 located along the surface of shaft 12 to enhance retention of access port 10 in tissue. In this embodiment, barbs 19 function as an anchoring member of an access port of the present disclosure. Barbs 19 may be made of any shape memory polymer or electroactive polymer described herein, and may be configured so that, prior to application of suitable energy, for example, while they are in their temporary state, they lie adjacent to or flush with the surface of shaft 12 thereby providing shaft 12 with a smooth, flat surface to facilitate insertion of access port 10 into tissue (not shown).

Figure 1B:
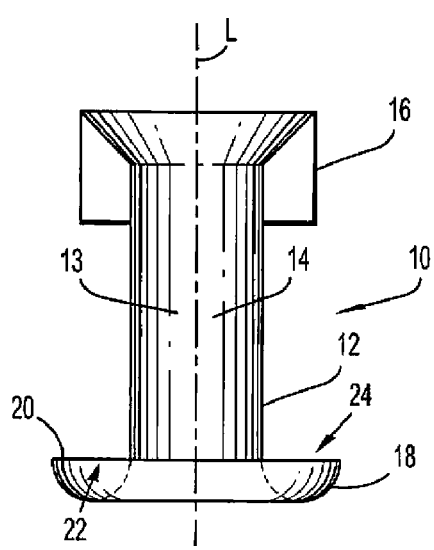

Upon application of suitable energy, such as heat or electricity, the shape memory material or electroactive polymer utilized to form distal end 18 will change to a permanent curved shape (i.e., the anchoring member) as depicted in FIG. 1B, thereby anchoring the access port 10 at the site of an incision. The distal-most end 20 of the curved shape of the anchoring member is circumferentially disposed about the longitudinal axis "L" such that the distal-most end 20 forms a monolithic ring 22 encircling a continuous path about the entire circumference of an outer diameter 13 of the shaft 12. The monolithic ring 22 is spaced apart from the shaft 12 by a circumferential trough 24 formed in the anchoring member. Similarly, as depicted in FIG. 1C, upon application of suitable energy, such as heat or electricity, the shape memory material or electroactive polymer utilized to form barbs 19 will form angular projections as their permanent shape as depicted in FIG. 1C, thereby anchoring the access port 10 at the site of an incision.

Figure 2A:
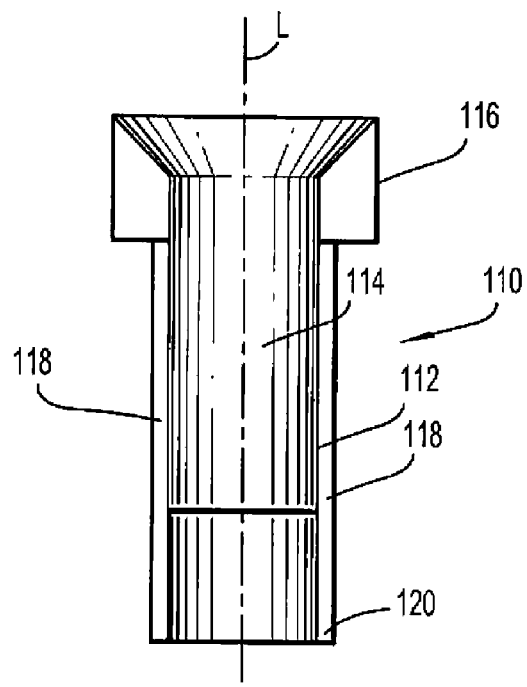
FIGS. 2A and 2B illustrate another access port of the present disclosure which has a material adhered thereto which alters its configuration upon the application of energy.

FIG. 2A illustrates an access port 110 of the present disclosure possessing a layer of material capable of altering its configuration thereby forming an anchoring member. The access port 110 possesses a longitudinally extending shaft 112 surrounding a central working passage 114. Proximal end 116 of access port 110 is wider than the distal end of access port 110. A layer 118 made of a material capable of changing its configuration is applied to an outer surface of shaft 112 so that the distal end 120 of layer 118 extends beyond the distal end of shaft 112. The distal end 120 of layer 118 changes its configuration upon the application of energy thereby forming an anchoring member. Materials which may be utilized to form layer 118 of shaft 112 include a shape memory material or electroactive polymer. As depicted in FIG. 2A, layer 118 possesses a straight, flat configuration thereby facilitating the insertion of access port 110 into tissue.

Figure 2B:
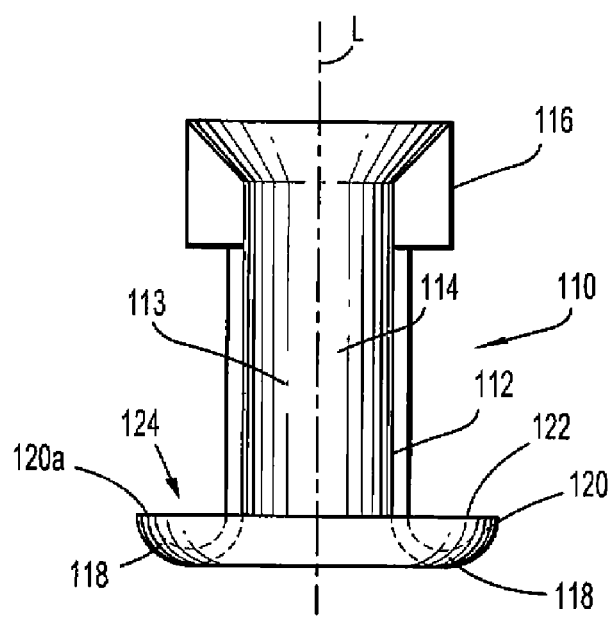

Upon application of suitable energy, such as heat or electricity, the distal end 120 of the shape memory material or electroactive polymer utilized to form layer 118 will change to a curved shape (i.e., the anchoring member) as depicted in FIG. 2B, thereby anchoring the access port 110 at the site of an incision. The distal-most end 120a of the curved shape of the anchoring member is circumferentially disposed about the longitudinal axis "L" such that the distal-most end 120a forms a monolithic ring 122 encircling a continuous path about the entire circumference of an outer diameter 113 of the shaft 112. The monolithic ring 122 is spaced apart from the shaft 112 by a circumferential trough 124 formed in the anchoring member.

Figure 3A:
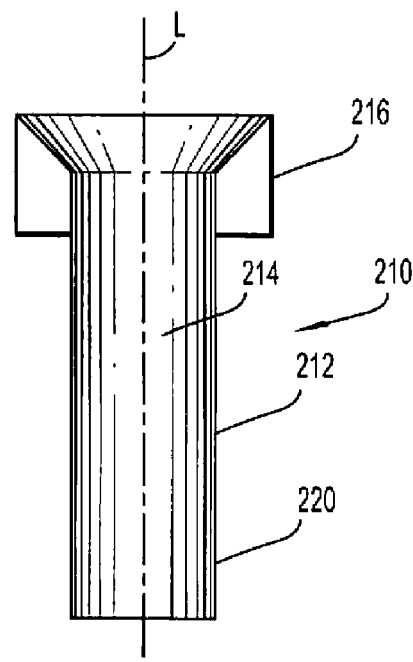
FIGS. 3A and 3B illustrate another access port of the present disclosure wherein the shaft of the access port is constructed of a material capable of altering its configuration upon the application of energy thereto.

FIG. 3A illustrates an access port 210 of the present disclosure possessing longitudinally extending shaft 212 surrounding a central working passage 214. Proximal end 216 of access port 210 is wider than the distal end of access port 210. Shaft 212 is formed of a material capable of altering its configuration thereby forming an anchoring member at its distal end 220. Materials which may be utilized to form shaft 212 include a shape memory material or electroactive polymer. As depicted in FIG. 3A, shaft 212 possesses a straight, flat configuration thereby facilitating the insertion of access port 210 into tissue.

Figure 3B:
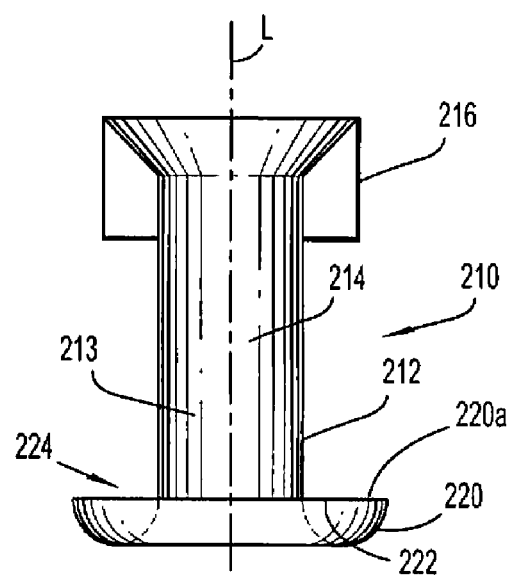

Upon application of suitable energy, such as heat or electricity, the distal end 220 of the shape memory material or electroactive polymer utilized to form shaft 212 will change to a curved shape (i.e., the anchoring member) as depicted in FIG. 3B, thereby anchoring the access port 210 at the site of an incision. The distal-most end 220a of the curved shape of the anchoring member is circumferentially disposed about the longitudinal axis "L" such that the distal-most end 220a forms a monolithic ring 222 encircling a continuous path about the entire circumference of an outer diameter 213 of the shaft 212. The monolithic ring 222 is spaced apart from the shaft 212 by a circumferential trough 224 formed in the anchoring member.

Once an access port has been secured to the site of an incision, an insufflation fluid or gas may by forced through the access port and into the body cavity and surgical instruments and similar devices may be introduced through the access port during a laparoscopic procedure.

In embodiments, it may be desirable to add additional components including medicinal agents with the shape memory polymers utilized to form the anchoring member found at the distal end of an access port of the present disclosure. The term "medicinal agent", as used herein, is used in its broadest sense and includes any substance or mixture of substances that have clinical use. Consequently, medicinal agents may or may not have pharmacological activity per se, e.g., a dye. Alternatively, a medicinal agent could be any agent which provides a therapeutic or prophylactic effect, a compound that affects or participates in tissue growth, cell growth, cell differentiation, a compound that may be able to invoke a biological action such as an immune response, or could play any other role in one or more biological processes.

Examples of classes of medicinal agents which may be utilized in accordance with the present disclosure include antimicrobials; analgesics; anesthetics; anti-inflammatory agents such as hormonal agents, hydrocortisone, prednisolone, prednisone, non-hormonal agents, allopurinol, indomethacin, phenylbutazone and the like; diagnostic agents; hemostats to halt or prevent bleeding; anticoagulants; antibiotics; anti-fungals; anti-virals; and immunological agents.

Suitable antimicrobial agents which may be included as a medicinal agent with the shape memory polymers utilized to form the anchoring member found at the distal end of an access port of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a medicinal agent with the shape memory polymers utilized to form the anchoring member of the present disclosure.

Examples of hemostat materials which can be employed include fibrin-based, collagen-based oxidized regenerated cellulose-based, and gelatin-based topical hemostats. Examples of commercially available hemostat materials include fibrinogen-thrombin combination materials sold under the trade designations CoStasis™ by Tyco Healthcare Group, LP, and Tisseel™ sold by Baxter International, Inc. Hemostats herein also include astringents, for example, aluminum sulfate, and coagulants.

A single medicinal agent may be utilized with the shape memory materials utilized to form the anchoring member found at the distal end of an access port of the present disclosure or, in alternate embodiments, any combination of medicinal agents may be utilized.

The medicinal agent may be disposed on a surface of the anchoring member found at the distal end of an access port, or impregnated in or combined with the shape memory materials utilized to form the anchoring member of an access port of the present disclosure.

Access ports of the present disclosure possessing an anchoring member at the distal end thereof made of shape memory materials or electroactive polymers may, in embodiments, avoid the need for extra deploying action, including that required with an anchoring balloon. The materials utilized to make the anchoring member are durable, the design is simple, and the access port with the anchoring member of the present disclosure is simple to make utilizing existing materials and manufacturing processes. Thus, the present disclosure provides an access port which is both economical and easy to use.

While the above description contains many specifics, these specifics should not be construed as limitations on the scope of the disclosure, but merely as exemplifications of embodiments thereof. Those skilled in the art will envision many other possibilities within the scope and spirit of the disclosure as defined by the claims appended hereto.

What is claimed is:

1. An access port comprising:
   a longitudinally extending shaft defining a longitudinal axis surrounding a central working passage; and
   at least one material capable of changing its configuration between a first condition and a second condition to form at least one anchoring member having a distal end circumferentially disposed about the longitudinal axis in the second condition such that the distal end of the at least one anchoring member forms a monolithic ring encircling a continuous path about the entire circumference of an outer diameter of the shaft, the ring being spaced apart from the shaft by a circumferential trough formed in the at least one anchoring member, the at least one material extending from a distal end of the shaft in both the first and second conditions, wherein a portion of the at least one anchoring member is disposed in angular relation relative to the longitudinal axis, and wherein the material is selected from the group consisting of shape memory polymers, shape memory metals, shape memory alloys, electroactive polymers, and combinations thereof.

2. The access port of claim 1, wherein the material capable of changing its configuration comprises a shape memory polymer selected from the group consisting of polyurethanes, poly(styrene-butadiene) block copolymers, polynorbornenes, caprolactones, dioxanones, diol esters, ether-ester diols, carbonates, and combinations thereof.

3. The access port of claim 1, wherein the material capable of changing its configuration comprises a shape memory polymer selected from the group consisting of oligo (epsilon caprolactone) diol, lactic acid, lactide, glycolic acid, glycolide, oligo (p-dioxanone) diol, trimethylene carbonate, and combinations thereof.

4. The access port of claim 1, wherein the material capable of changing its configuration comprises a shape memory polymer selected from the group consisting of poly(styrene-butadiene) copolymers, oligo (epsilon caprolactone) diollo-ligo (p-dioxanone) diol copolymers, and poly(epsilon-caprolactone) dimethacrylate-poly (n-butyl acrylate) copolymers.

5. The access port of claim 1, wherein the material capable of changing its configuration comprises a shape memory polymer comprising a blend of materials selected from the group consisting of urethanes, lactic acid, glycolic acid, acrylates, caprolactones, homopolymers thereof, copolymers thereof, and combinations thereof.

6. The access port of claim 1, wherein the material capable of changing its configuration comprises a shape memory polymer which undergoes a change in shape at a temperature from about 30° C. to about 50° C.

7. The access port of claim 1, wherein the material capable of changing its configuration comprises an electroactive polymer selected from the group consisting of poly(aniline), substituted poly(aniline)s, polycarbazoles, substituted polycarbazoles, polyindoles, poly(pyrrole)s, substituted poly(pyrrole)s, poly(thiophene)s, substituted poly(thiophene)s, poly(acetylene)s, polyethylene dioxythiophene)s, poly(ethylenedioxypyrrole)s, poly(p-phenylene vinylene)s, and combinations thereof.

8. The access port of claim 1, wherein the material capable of changing its configuration comprises an electroactive polymer which undergoes a change in shape upon the application of electricity in amounts from about 5 volts to about 30 volts.

9. The access port of claim 1, wherein the material capable of changing its configuration is secured to the distal end of the shaft.

10. The access port of claim 9, wherein the material capable of changing its configuration is secured to the distal end of the shaft by at least one of chemical methods and physical methods.

11. The access port of claim 9, wherein the material capable of changing its configuration is chemically secured to the distal end of the shaft by at least one of adhesives, sealants, and glues.

12. The access port of claim 9, wherein the material capable of changing its configuration is physically secured to the distal end of the shaft by locking rings located on the proximal end and distal end of the anchoring member.

13. The access port of claim 9, wherein the material capable of changing its configuration is applied to an outer surface of the shaft as a layer.

14. The access port of claim 1, wherein the anchoring member has a permanent shape comprising a curved shape and a temporary shape comprising a straight shape.

15. The access port of claim 1, wherein the shaft itself is formed of the material capable of changing its configuration.

16. The access port of claim 1, wherein the anchoring member further comprises a medicinal agent.

17. The access port of claim 1, wherein the central working passage is configured to receive a surgical instrument in a substantially sealed relationship therewith.

18. The access port of claim 1, wherein at least one anchoring member is disposed proximal a second anchoring member along the longitudinal axis.

* * * * *